(12) United States Patent
Deborski et al.

(10) Patent No.: US 8,093,500 B2
(45) Date of Patent: Jan. 10, 2012

(54) MICROWAVE CABLE COOLING

(75) Inventors: Christopher A. Deborski, Denver, CO (US); Darion Peterson, Boulder, CO (US)

(73) Assignee: Vivant Medical, Inc., Boulder, CO (US)

( * ) Notice: Subject to any disclaimer, the term of this patent is extended or adjusted under 35 U.S.C. 154(b) by 0 days.

(21) Appl. No.: 12/814,787

(22) Filed: Jun. 14, 2010

(65) Prior Publication Data

US 2010/0243287 A1 Sep. 30, 2010

Related U.S. Application Data

(62) Division of application No. 11/820,193, filed on Jun. 18, 2007, now Pat. No. 7,777,130.

(51) Int. Cl.
*H01R 4/00* (2006.01)
(52) U.S. Cl. .................................................. 174/92
(58) Field of Classification Search .................. 174/15.1, 174/110 R, 102 R, 74 R, 84 R, 91, 92, 93; 29/825–828
See application file for complete search history.

(56) References Cited

U.S. PATENT DOCUMENTS

| | | | |
|---|---|---|---|
| 2,029,420 A | 2/1936 | Green | |
| 2,165,961 A | 7/1939 | Cork et al. | |
| 2,510,358 A | 6/1950 | Wolf | |
| 3,060,210 A * | 10/1962 | De Groote et al. | 507/244 |
| 3,634,606 A | 1/1972 | Iyengar | |
| 3,777,371 A | 12/1973 | Iyengar et al. | |
| 3,885,083 A | 5/1975 | Jachimowicz et al. | |
| 3,893,355 A | 7/1975 | Maastricht | |
| 3,943,470 A | 3/1976 | Bingham | |
| 4,092,485 A | 5/1978 | Wanser | |
| 4,143,649 A | 3/1979 | Foti | |
| 4,198,828 A | 4/1980 | Mercier et al. | |
| D263,020 S | 2/1982 | Rau, III | |
| 4,377,547 A | 3/1983 | Hervig | |
| 4,415,763 A | 11/1983 | Cookson | |
| 4,493,710 A | 1/1985 | King et al. | |
| 4,648,919 A * | 3/1987 | Diaz et al. | 156/48 |
| D295,893 S | 5/1988 | Sharkany et al. | |
| D295,894 S | 5/1988 | Sharkany et al. | |
| 4,865,123 A | 9/1989 | Kawashima et al. | |
| 4,977,547 A * | 12/1990 | Giniewicz et al. | 367/157 |
| 5,048,598 A | 9/1991 | Takemae et al. | |
| 5,147,161 A | 9/1992 | Whiting | |
| 5,190,421 A | 3/1993 | Wen et al. | |

(Continued)

FOREIGN PATENT DOCUMENTS

CN 1103807 6/1995

(Continued)

OTHER PUBLICATIONS

U.S. Appl. No. 08/483,742, filed Jun. 7, 1995.

(Continued)

*Primary Examiner* — William Mayo, III

(57) ABSTRACT

A cable cooling apparatus, for dissipating heat generated by a cable, includes a housing disposed on a portion of a cable and defining a fluid-tight cavity therewithin. The housing is configured to cool at least a portion of the cable. The housing also includes one or more inlets, configured to receive fluid in the housing, and one or more outlets in fluid communication with an inlet for discharging the fluid from the housing. The fluid enters the housing through an inlet, circulates through a portion of the housing and absorbs thermal energy from a portion of the cable.

10 Claims, 9 Drawing Sheets

U.S. PATENT DOCUMENTS

| | | | |
|---|---|---|---|
| 5,312,658 A * | 5/1994 | Griffith | 428/34.4 |
| 5,334,193 A | 8/1994 | Nardella | |
| 5,348,554 A | 9/1994 | Imran et al. | |
| 5,358,515 A | 10/1994 | Hurter et al. | |
| 5,535,818 A | 7/1996 | Fujisaki et al. | |
| 5,620,440 A | 4/1997 | Heckele et al. | |
| 5,703,536 A | 12/1997 | Davis et al. | |
| 5,843,021 A | 12/1998 | Edwards et al. | |
| 5,951,216 A | 9/1999 | Antoun | |
| 5,951,546 A | 9/1999 | Lorentzen | |
| 6,007,571 A | 12/1999 | Neilson et al. | |
| D424,694 S | 5/2000 | Tetzlaff et al. | |
| D425,201 S | 5/2000 | Tetzlaff et al. | |
| 6,106,504 A | 8/2000 | Urrutia | |
| 6,112,813 A * | 9/2000 | Head | 166/302 |
| 6,134,476 A | 10/2000 | Arndt et al. | |
| 6,149,677 A | 11/2000 | Dobak, III | |
| 6,259,067 B1 | 7/2001 | Faries, Jr. et al. | |
| 6,259,074 B1 | 7/2001 | Brunner et al. | |
| D449,886 S | 10/2001 | Tetzlaff et al. | |
| 6,348,049 B1 | 2/2002 | Spencer | |
| 6,355,024 B1 | 3/2002 | Small et al. | |
| 6,371,157 B1 | 4/2002 | See et al. | |
| RE37,704 E | 5/2002 | Eshel | |
| D457,958 S | 5/2002 | Dycus et al. | |
| D457,959 S | 5/2002 | Tetzlaff et al. | |
| 6,383,180 B1 | 5/2002 | Lalonde et al. | |
| 6,468,258 B1 | 10/2002 | Shang | |
| 6,506,189 B1 | 1/2003 | Rittman, III et al. | |
| 6,524,308 B1 | 2/2003 | Muller et al. | |
| 6,530,922 B2 | 3/2003 | Cosman et al. | |
| 6,575,969 B1 | 6/2003 | Rittman, III et al. | |
| 6,577,903 B1 | 6/2003 | Cronin et al. | |
| 6,592,577 B2 | 7/2003 | Abboud et al. | |
| 6,623,455 B2 | 9/2003 | Small et al. | |
| 6,635,053 B1 | 10/2003 | Lalonde et al. | |
| 6,682,525 B2 | 1/2004 | Lalonde et al. | |
| 6,706,040 B2 | 3/2004 | Mahon et al. | |
| 6,723,094 B1 | 4/2004 | Desinger | |
| D496,997 S | 10/2004 | Dycus et al. | |
| D499,181 S | 11/2004 | Dycus et al. | |
| 6,818,000 B2 | 11/2004 | Muller et al. | |
| 6,847,848 B2 | 1/2005 | Sterzer et al. | |
| 6,849,063 B1 | 2/2005 | Eshel et al. | |
| 6,881,214 B2 | 4/2005 | Cosman et al. | |
| 6,893,419 B2 | 5/2005 | Noda et al. | |
| 6,942,661 B2 | 9/2005 | Swanson | |
| 6,953,461 B2 | 10/2005 | McClurken et al. | |
| 6,956,164 B2 | 10/2005 | Brown | |
| 7,041,095 B2 | 5/2006 | Wang et al. | |
| D525,361 S | 7/2006 | Hushka | |
| D531,311 S | 10/2006 | Guerra et al. | |
| D533,942 S | 12/2006 | Kerr et al. | |
| D535,027 S | 1/2007 | James et al. | |
| D541,418 S | 4/2007 | Schechter et al. | |
| D541,938 S | 5/2007 | Kerr et al | |
| 7,282,638 B2 | 10/2007 | Karlsen et al. | |
| 7,303,554 B2 | 12/2007 | Lalonde et al. | |
| 7,311,703 B2 | 12/2007 | Turovskiy et al. | |
| D564,662 S | 3/2008 | Moses et al. | |
| 7,377,917 B2 | 5/2008 | Trembly | |
| D613,412 S | 4/2010 | DeCarlo | |
| 2005/0065584 A1 | 3/2005 | Schiff et al. | |
| 2005/0149010 A1 | 7/2005 | Turovskiy et al. | |
| 2005/0245920 A1 | 11/2005 | Vitullo et al. | |
| 2006/0243471 A1 * | 11/2006 | Karlsen et al. | 174/15.1 |
| 2008/0308256 A1 | 12/2008 | Deborski et al. | |
| 2010/0210129 A1 | 8/2010 | Arts et al. | |
| 2010/0217251 A1 | 8/2010 | Rossetto et al. | |
| 2010/0217252 A1 | 8/2010 | Rossetto et al. | |

FOREIGN PATENT DOCUMENTS

| | | |
|---|---|---|
| DE | 390937 | 3/1924 |
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10310765 | 9/2004 |
| DE | 10328514 | 3/2005 |
| DE | 102004022206 | 12/2005 |
| DE | 202005015147 | 3/2006 |
| EP | 0 246 350 | 11/1987 |
| EP | 0 521 264 | 1/1993 |
| EP | 0 556 705 | 8/1993 |
| EP | 0 558 429 | 9/1993 |
| EP | 0 836 868 | 4/1998 |
| EP | 0 882 955 | 12/1998 |
| EP | 1 159 926 | 5/2001 |
| FR | 179 607 | 11/1906 |
| FR | 1 275 415 | 9/1960 |
| FR | 1 347 865 | 11/1963 |
| FR | 2 276 027 | 6/1974 |
| FR | 2 235 669 | 1/1975 |
| FR | 2 313 708 | 12/1976 |
| FR | 2 502 935 | 10/1982 |
| FR | 2 517 953 | 6/1983 |
| FR | 2 573 301 | 11/1984 |
| FR | 2 862 813 | 5/2005 |
| FR | 2 864 439 | 7/2005 |
| JP | 5-5106 | 1/1993 |
| JP | 05-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09000492 | 1/1997 |
| JP | 09010223 | 1/1997 |
| JP | 11244298 | 9/1999 |
| JP | 2000342599 | 12/2000 |
| JP | 2000350732 | 12/2000 |
| JP | 2001008944 | 1/2001 |
| JP | 2001029356 | 2/2001 |
| JP | 2001128990 | 5/2001 |
| JP | 2001231870 | 8/2001 |
| JP | 2008142467 | 6/2008 |
| SU | 166452 | 11/1964 |
| SU | 401367 | 11/1974 |
| SU | 727201 | 4/1980 |
| WO | WO2010/035831 | 4/2010 |

OTHER PUBLICATIONS

U.S. Appl. No. 08/136,098, filed Oct. 14, 1993.

U.S. Appl. No. 12/401,268, filed Mar. 10, 2009.
U.S. Appl. No. 12/416,583, filed Apr. 1, 2009.
U.S. Appl. No. 12/423,609, filed Apr. 14, 2009.
U.S. Appl. No. 12/436,231, filed May 6, 2009.
U.S. Appl. No. 12/436,237, filed May 6, 2009.
U.S. Appl. No. 12/436,239, filed May 6, 2009.
U.S. Appl. No. 12/472,831, filed May 27, 2009.
U.S. Appl. No. 12/475,082, filed May 29, 2009.
U.S. Appl. No. 12/476,960, filed Jun. 2, 2009.
U.S. Appl. No. 12/487,917, filed Jun. 19, 2009.
U.S. Appl. No. 12/493,302, filed Jun. 29, 2009.
U.S. Appl. No. 12/504,738, filed Jul. 17, 2009.
U.S. Appl. No. 12/535,851, filed Aug. 5, 2009.
U.S. Appl. No. 12/535,856, filed Aug. 5, 2009.
U.S. Appl. No. 12/536,616, filed Aug. 6, 2009.
U.S. Appl. No. 12/542,348, filed Aug. 17, 2009.
U.S. Appl. No. 12/542,785, filed Aug. 18, 2009.
U.S. Appl. No. 12/547,155, filed Aug. 25, 2009.
U.S. Appl. No. 12/548,644, filed Aug. 27, 2009.
U.S. Appl. No. 12/555,576, filed Sep. 8, 2009.
U.S. Appl. No. 12/556,010, filed Sep. 9, 2009.
U.S. Appl. No. 12/556,238, filed Sep. 9, 2009.
U.S. Appl. No. 12/561,096, filed Sep. 16, 2009.
U.S. Appl. No. 12/562,575, filed Sep. 18, 2009.
U.S. Appl. No. 12/562,842, filed Sep. 18, 2009.
U.S. Appl. No. 12/566,299, filed Sep. 24, 2009.
U.S. Appl. No. 12/568,067, filed Sep. 28, 2009.
U.S. Appl. No. 12/568,524, filed Sep. 28, 2009.
U.S. Appl. No. 12/568,551, filed Sep. 28, 2009.
U.S. Appl. No. 12/568,777, filed Sep. 29, 2009.
U.S. Appl. No. 12/568,838, filed Sep. 29, 2009.
U.S. Appl. No. 12/568,883, filed Sep. 29, 2009.
U.S. Appl. No. 12/568,972, filed Sep. 29, 2009.
U.S. Appl. No. 12/569,171, filed Sep. 29, 2009.
U.S. Appl. No. 12/569,685, filed Sep. 29, 2009.
U.S. Appl. No. 12/582,857, filed Oct. 21, 2009.
U.S. Appl. No. 12/606,769, filed Oct. 27, 2009.
U.S. Appl. No. 12/607,221, filed Oct. 28, 2009.
U.S. Appl. No. 12/607,268, filed Oct. 28, 2009.
U.S. Appl. No. 12/619,323, filed Nov. 16, 2009.
U.S. Appl. No. 12/619,462, filed Nov. 16, 2009.
U.S. Appl. No. 12/620,289, filed Nov. 17, 2009.
U.S. Appl. No. 12/642,623, filed Dec. 18, 2009.
U.S. Appl. No. 12/686,726, filed Jan. 13, 2010.
U.S. Appl. No. 12/692,856, filed Jan. 25, 2010.
U.S. Appl. No. 12/696,671, filed Jan. 29, 2010.
U.S. Appl. No. 12/696,966, filed Jan. 29, 2010.
U.S. Appl. No. 12/701,030, filed Feb. 5, 2010.
U.S. Appl. No. 12/708,974, filed Feb. 19, 2010.
U.S. Appl. No. 12/709,014, filed Feb. 19, 2010.
U.S. Appl. No. 12/712,864, filed Feb. 25, 2010.
U.S. Appl. No. 12/713,429, filed Feb. 26, 2010.
U.S. Appl. No. 12/713,515, filed Feb. 26, 2010.
U.S. Appl. No. 12/713,641, filed Feb. 26, 2010.
U.S. Appl. No. 12/722,034, filed Mar. 11, 2010.
U.S. Appl. No. 12/731,367, filed Mar. 25, 2010.
U.S. Appl. No. 12/732,508, filed Mar. 26, 2010.
U.S. Appl. No. 12/732,521, filed Mar. 26, 2010.
U.S. Appl. No. 12/761,267, filed Apr. 15, 2010.
U.S. Appl. No. 12/772,675, filed May 3, 2010.
U.S. Appl. No. 12/777,984, filed May 11, 2010.
U.S. Appl. No. 12/786,671, filed May 25, 2010.
U.S. Appl. No. 12/787,639, filed May 26, 2010.
U.S. Appl. No. 12/792,904, filed Jun. 3, 2010.
U.S. Appl. No. 12/792,932, filed Jun. 3, 2010.
U.S. Appl. No. 12/792,947, filed Jun. 3, 2010.
U.S. Appl. No. 12/792,970, filed Jun. 3, 2010.
U.S. Appl. No. 12/793,037, filed Jun. 3, 2010.
U.S. Appl. No. 12/819,330, filed Jun. 21, 2010.
U.S. Appl. No. 12/823,211, filed Jun. 25, 2010.
U.S. Appl. No. 12/826,902, filed Jun. 30, 2010.

Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With the LigaSure™ Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 94 In Biologic Effects of Nonionizing Electromagnetic Fields, CRC Press, Inc., pp. 1424-1428.
Chung et al., "Clinical Experience of Sutureless Closed Hemorrhoidectomy with LigaSure™" Diseases of the Colon & Rectum, vol. 46, No. 1, Jan. 2003.
Cosman et al., "Methods of Making Nervous System Lesions" in William RH, Rengachary SS (eds): Neurosurgery, New York: McGraw Hill, vol. 111, (1984), pp. 2490-2499.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15:(1984), pp. 945-950.
Crawford et al., "Use of the LigaSure™ Vessel Sealing System in Urologic Cancer Surger" Grand Rounds in Urology 1999, vol. 1, Issue 4, pp. 1 0-17.
Dulemba et al., "Use of a Bipolar Electrothermal Vessel Sealer in Laparoscopically Assisted Vaginal Hysterectomy" Sales/Product Literature; Jan. 2004.

E. David Crawford, "Evaluation of a New Vessel Sealing Device in Urologic Cancer Surgery" Sales/Product Literature 2000.

E. David Crawford, "Use of a Novel Vessel Sealing Technology in Management of the Dorsal Veinous Complex" Sales/Product Literature 2000.

Esterline, "Light Key Projection Keyboard" 2004 Advanced Input Systems, located at: <http://www.advanced-input.com/lightkey> last visited on Feb. 10, 2005.

Esterline Product Literature, "Light Key: Visualize a Virtual Keyboard. One With No Moving Parts", Nov. 1, 2003; 4 pages.

Geddes et al., "The Measurement of Physiologic Events by Electrical Impedence" Am. J. MI, Jan. Mar. 1964, pp. 16-27.

Goldberg et al., "Image-guided Radiofrequency Tumor Ablation: Challenges and Opportunities—Part I", (2001) J Vasc. Interv. Radiol, vol. 12, pp. 1021-1032.

Goldberg et al. (1995) "Saline-enhanced RF Ablation: Demonstration of Efficacy and Optimization of Parameters", Radiology, 197(P): 140 (Abstr).

Goldberg et al., "Tissue Ablation with Radiofrequency: Effect of Probe Size, Gauge, Duration, and Temperature on Lesion Volume" Acad Radio (1995) vol. 2, No. 5, pp. 399-404.

H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.

Heniford et al., "Initial Results with an Electrothermal Bipolar Vessel Sealer" Surgical Endoscopy (2001) 15:799-801.

Herman at al., "Laparoscopic Intestinal Resection With the LigaSure™ Vessel Sealing System: A Case Report" Innovations That Work, Feb. 2002.

Humphries Jr. et al., "Finite Element Codes to Model Electrical Heating and Nonlinear Thermal Transport in Biological Media", Proc. ASME HTD-355, 131 (1997).

Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.

Jarrett et al., "Use of the LigaSure™ Vessel Sealing System for Peri-Hilar Vessels in Laparoscopic Nephrectomy" Sales/Product Literature 2000.

Johnson et al., "Evaluation of a Bipolar Electrothermal Vessel Sealing Device in Hemorrhoidectomy" Sales/Product Literature, Jan. 2004.

Johnson, "Evaluation of the LigaSure™ Vessel Sealing System in Hemorrhoidectormy" American College of Surgeons (ACS) Clinic La Congress Poster (2000).

Johnson et al., "New Low-Profile Applicators for Local Heating of Tissues", IEEE Transactions on Biomedical Engineering, vol., BME-31, No. 1, Jan. 1984, pp. 28-37.

Johnson, "Use of the LigaSure™ Vessel Sealing System in Bloodless Hemorrhoidectomy" Innovations That Work, Mar. 2000.

Joseph G. Andriole M.D. et al., "Biopsy Needle Characteristics Assessed in the Laboratory", Radiology 148: 659-662, Sep. 1983.

Joseph Ortenberg, "LigaSure™ System Used in Laparoscopic 1st and 2nd Stage Orchiopexy" Innovations That Work, Nov. 2002.

K. Ogata, Modern Control Engineering, Prentice-Hall, Englewood Cliffs, N.J., 1970.

Kennedy et al., "High-burst-strength, feedback-controlled bipolar vessel sealing" Surgical Endoscopy (1998) 12: 876-878.

Kopans, D.B. et al., (Nov. 1985) "Spring Hookwire Breast Lesion Localizer: Use with Rigid-Compression. Mammographic Systems," Radiology 157(2):537-538.

Koyle et al., "Laparoscopic Palomo Varicocele Ligation in Children and Adolescents" Pediatric Endosurgery & Innovative Techniques, vol. 6, No. 1, 2002.

Muller et al., "Extended Left Hemicolectomy Using the LigaSure™ Vessel Sealing System" Innovations That Work. LJ, Sep. 1999.

Murakami, R. et al., (1995). "Treatment of Hepatocellular Carcinoma: Value of Percutaneous Microwave Coagulation," American Journal of Radiology (AJR) 164:1159-1164.

Ni Wei et al., "A Signal Processing Method for the Coriolis Mass Flowmeter Based on a Normalized . . . " Journal of Applied Sciences Yingyong Kexue Xuebao, Shangha CN, vol. 23, No. 2:(Mar. 2005); pp. 160-184.

Ogden, "Goertzel Alternative to the Fourier Transform" Jun. 1993 pp. 485-487 Electronics World; Reed Business Publishing, Sutton, Surrey, BG, vol. 99, No. 9, 1687.

Olsson M.D. et al., "Radical Cystectomy in Females" Current Surgical Techniques in Urology, vol. 14, Issue 3, 2001.

Organ, L W., "Electrophysiologic Principles of Radiofrequency Lesion Making" Appl. Neurophysiol, vol. 39: pp. 69-76 (1976/77).

P.R. Stauffer et al., "Interstitial Heating Technologies", Thermoradiotheray and Thermochemotherapy (1995) vol. 1, Biology, Physiology, Physics, pp. 279-320.

Palazzo et al., "Randomized clinical trial of LigaSure™ versus open haemorrhoidectomy" British Journal of Surgery 2002,89,154-157 "Innovations in Electrosurgery" Sales/Product Literature; Dec. 31, 2000.

Paul G. Horgan, "A Novel Technique for Parenchymal Division During Hepatectomy" The American Journal of Surgery, vol. 181, No. 3, Apr. 2001, pp. 236-237.

Peterson et al., "Comparison of Healing Process Following Ligation with Sutures and Bipolar Vessel Sealing" Surgical Technology International (2001).

R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.

Valleylab Brochure, "Reducing Needlestick Injuries in the Operating Room" 1 page, Mar. 2001.

Reidenbach, (1995) "First Experimental Results with Special Applicators for High-Frequency Interstitial Thermotherapy", Society Minimally Invasive Therapy, 4(Suppl 1):40 (Abstr).

Richard Wolf Medical Instruments Corp. Brochure, "Kleppinger Bipolar Forceps & Bipolar Generator" 3 pages, Jan. 1989.

Rothenberg et al., "Use of the LigaSure™ Vessel Sealing System in Minimally Invasive Surgery in Children" Int'l Pediatric Endosurgery Group (I PEG) 2000.

Sayfan et al., "Sutureless Closed Hemorrhoidectomy: A New Technique" Annals of Surgery, vol. 234, No. 1, Jul. 2001, pp. 21-24.

Sengupta et al., "Use of a Computer-Controlled Bipolar Diathermy System in Radical Prostatectomies and Other Open Urological Surgery" ANZ Journal of Surgery (2001) 71.9 pp. 538-540.

Sigel et al., "The Mechanism of Blood Vessel Closure by High Frequency Electrocoagulation" Surgery Gynecology & Obstetrics, Oct. 1965 pp. 823-831.

Solbiati et al., (2001) "Percutaneous Radio-frequency Ablation of Hepatic Metastases from Colorectal Cancer: Long-term Results in 117 Patients", Radiology, vol. 221, pp. 159-166.

Solbiati et al. (1995) "Percutaneous US-guided RF Tissue Ablation of Liver Metastases: Long-term Follow-up", Radiology, pp. 195-203.

Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.

Stuart W. Young, Nuclear Magnetic Resonance Imaging—Basic Principles, Raven Press, New York, 1984.

Sugita et al., "Bipolar Coagulator with Automatic Thermocontrol" J. Neurosurg., vol. 41, Dec. 1944, pp. 777-779.

Sylvain Labonte et al., "Monopole Antennas for Microwave Catheter Ablation", IEEE Trans. on Microwave Theory and Techniques, vol. 44, No. 10, pp. 1832-1840, Oct. 1995.

T. Matsukawa et al., "Percutaneous Microwave Coagulation Therapy in Liver Tumors", Acta Radiologica, vol. 38, pp. 410-415, 1997.

T. Seki et al., (1994) "Ultrasonically Guided Percutaneous Microwave Coagulation Therapy for Small Hepatocellular Carcinoma," Cancer 74(3):817-825.

Urologix, Inc.—Medical Professionals: Targis™ Technology (Date Unknown). "Overcoming the Challenge" located at: <http://www.urologix.com/medicaUtechnology.html > last visited on Apr. 27, 2001, 3 pages.

Urrutia et al., (1988). "Retractable-Barb Needle for Breast Lesion Localization: Use in 60 Cases," Radiology 169(3):845-847.

Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation—'COA-COMP'" Neurosurgical Review 7:2-3 (1984) pp. 187-190.
W. Scott Helton, "LigaSure™ Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 02786604.5 dated Feb. 10, 2010.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 04778192.7 dated Jul. 1, 2009.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Jul. 25, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2007.
European Search Report EP 07015601.3 dated Jan. 4, 2007.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08011282 dated Aug. 14, 2009.
European Search Report EP 08011705 dated Aug. 20, 2009.
European Search Report EP 08011705.4 extended dated Nov. 4, 2009.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08020530.5 dated May 27, 2009.
European Search Report EP 08169973.8 dated Apr. 6, 2009.
European Search Report EP 09010873.9 extended dated Nov. 13, 2009.
European Search Report EP 09010877.0 extended dated Dec. 3, 2009.
European Search Report EP 09151621 dated Jun. 18, 2009.
European Search Report EP 09156861.8 dated Aug. 4, 2009.
European Search Report EP 09161502.1 dated Sep. 2, 2009.
European Search Report EP 09161502.1 extended dated Oct. 30, 2009.
European Search Report EP 09165976.3 extended dated Mar. 17, 2010.
European Search Report EP 09166708 dated Oct. 15, 2009.
European Search Report EP 09166708.9 dated Mar. 18, 2010.
European Search Report EP 09169376.2 extended dated Dec. 16, 2009.
European Search Report EP 09172188.6 extended dated Apr. 23, 2010.
European Search Report EP 09172838.6 extended dated Jan. 20, 2010.
European Search Report EP 09173268.5 extended dated Jan. 27, 2010.

European Search Report EP 10158944.8 extended dated Jun. 21, 2010.
European Search Report EP 10161722.3 extended dated Jun. 16, 2010.
International Search Report PCT/US98/18640 dated Jan. 29, 1998.
International Search Report PCT/US98/23950 dated Jan. 14, 1998.
International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2004.
International Search Report PCT/US05/36168 dated Aug. 28, 2006.
International Search Report PCT/US08/052460 dated Apr. 24, 2008.
International Search Report PCT/US09/31658 dated Mar. 11, 2009.

* cited by examiner

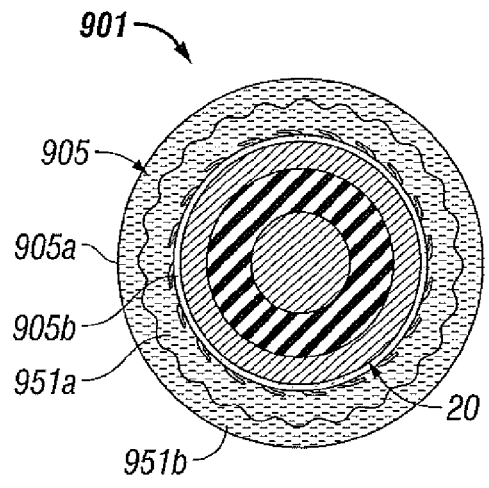
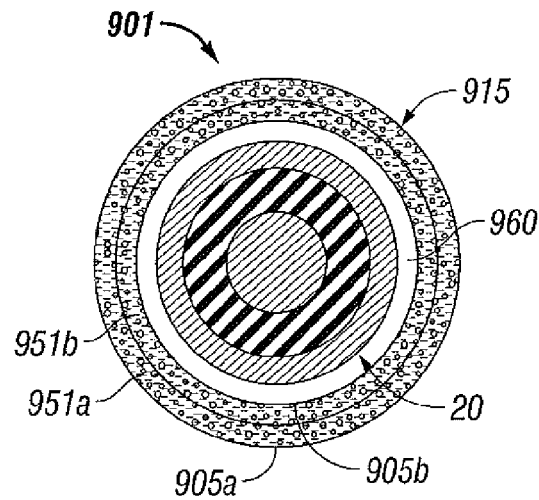
FIG. 10A　　　　　FIG. 10B
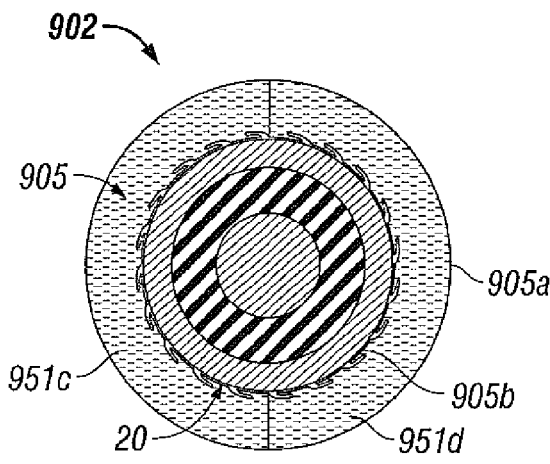
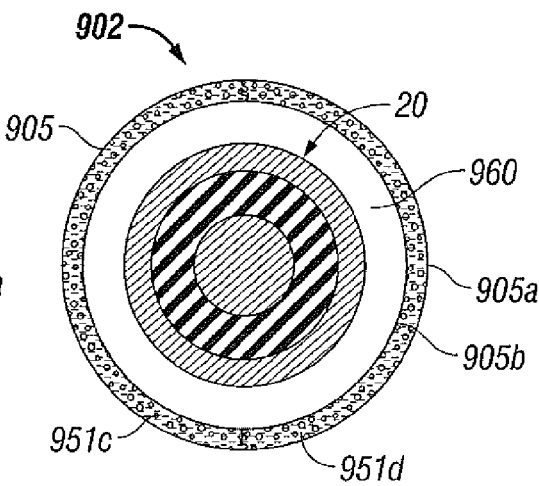
FIG. 10C　　　　　FIG. 10D

MICROWAVE CABLE COOLING

CROSS-REFERENCE TO RELATED APPLICATIONS

The present application is a Divisional Application which claims the benefit of and priority to U.S. patent application Ser. No. 11/820,193, filed on Jun. 18, 2007, now U.S. Pat. No. 7,777,130, the entire content of which is incorporated herein by reference.

BACKGROUND

1. Technical Field

The present disclosure relates generally to energy transmission for medical/surgical ablation devices and assemblies and methods of their use. More particularly, the present disclosure relates to cooling microwave energy transmission cables that deliver microwave energy to microwave antenna devices and assemblies.

2. Background of Related Art

In the treatment of diseases such as cancer, certain types of cancer cells have been found to denature at elevated temperatures (which are slightly lower than temperatures normally injurious to healthy cells). These types of treatments, known generally as hyperthermia therapy, typically utilize electromagnetic radiation to heat diseased cells to temperatures above 41° C. The body may maintain healthy cells adjacent the diseased tissue at a lower temperatures where irreversible cell destruction will not occur by maintaining sufficient blood flow. Other procedures utilizing electromagnetic radiation to heat tissue also include ablation and coagulation of the tissue. Such microwave ablation procedures, e.g., such as those performed for menorrhagia, are typically done to ablate and coagulate the targeted tissue to denature or kill it. Many procedures and types of devices utilizing electromagnetic radiation therapy are known in the art. Such microwave therapy is typically used in the treatment of tissue and organs such as the kidney, lung, prostate, heart, and liver.

One minimally invasive procedure generally involves the treatment of tissue (e.g., a tumor) underlying the skin via the use of microwave energy. Tissue may be accessed percutaneously, or through the skin, and the microwave energy further penetrates the adjacent tissue to ablate large areas of tissue. However, treatment with microwave energy requires the transmission of energy at microwave frequencies from an electrosurgical generator to an ablation device and the transmission often results in problems such as inadvertent discharge of microwave energy and/or transmission line heating.

Although there are various means for transmitting microwave energy, the most common means in medical ablation involves use of a coaxial cable. While high quality coaxial cables are designed and manufactured to minimize and/or eliminate inadvertent discharge of microwave energy all coaxial cable experiences a temperature increase while delivering microwave energy.

The present disclosure describes a coaxial cable cooling apparatus including a housing with various active and passive cooling means and methods.

SUMMARY

The present disclosure relates generally to energy transmission for medical/surgical ablation devices and assemblies and methods of their use. More particularly, the present disclosure relates to cooling microwave energy transmission cables that deliver the microwave energy to microwave antenna devices and assemblies.

A cable cooling apparatus, for dissipating heat generated by a cable, includes a housing and a meltable material. The housing is configured for attachment to at least a portion of a cable and configured to retain the meltable material. The meltable material, disposed within the housing, is configured to dissipate thermal energy from the cable during transformation to a second state. The temperature at which the material transforms from a first state to a second state may be between about 40° C. and about 100° C. The meltable material may be selected from a group consisting of animal wax, insect wax, vegetable wax, mineral wax, petroleum wax, synthetic wax and an evaporative material. The coaxial cable may be a microwave energy transmission cable.

In a further embodiment of the present disclosure the housing may further include at least one inlet and one outlet formed in the housing. The at least one inlet may be in fluid communication with the meltable material and configured to receive a fluid. The at least one outlet may be in fluid communication with at least one of the inlets and configured to discharge the fluid from the housing. The fluid may be a thermally conductive fluid and may be selected from a group consisting of water, saline, ammonium chloride, sodium nitrate, and potassium chloride. The cable may be a microwave energy transmission cable.

In another embodiment of the present disclosure, cable cooling apparatus, for dissipating heat generated by a cable, includes a housing defining a fluid-tight cavity therewithin, the housing disposed on at least a portion of a cable and configured to cool at least a portion of the cable. The housing includes at least one inlet configured to receive a fluid for cooling and at least one outlet, in fluid communication with the at least one inlet, for discharging the fluid from the housing. The fluid enters the housing through the inlet, is circulated through at least a portion of the housing and absorbs thermal energy from at least a portion of the cable. The housing may surround at least a portion of the cable.

In a further embodiment of the present invention the housing may further include a cooling portion in thermal communication with the cable and a return portion for returning fluid through the at least one outlet. The cooling portion and the return portion may be formed of one of a multi-lumen tube, two or more paratubes, and a concentrically orientated multi-lumen tube. The coaxial cable may be a microwave transmission cable and the housing may be in direct contact with the outer conductor of the coaxial cable.

In yet another embodiment of the present disclosure a method for cooling a microwave energy transmission cable during energy transmission through the cable is provided. The method includes the steps of positioning at least one cable cooling apparatus adjacent a microwave energy transmission cable; transmitting energy through the energy transmission cable; and dissipating heat produced by the energy transmission cable, during the energy transmission, through the at least one cable cooling apparatus.

The cable cooling apparatus may include a plurality of cable cooling apparatus along the microwave energy transmission cable. The cable cooling apparatus may contain a selectively meltable material configured to dissipate heat from the microwave energy transmission cable. When heated, the meltable material may change from a first state to a second state.

In a further embodiment of the present disclosure the method may include the steps of providing a cooling fluid to the at least one cable cooling apparatus and circulating the fluid therethrough.

BRIEF DESCRIPTION OF THE DRAWINGS

FIG. 10A is a transverse cross-sectional view of one embodiment of the cooling sleeve apparatus of FIG. 9 with a cooling body filled with fluid and pressed against the coaxial cable;

FIG. 10B is a transverse cross-sectional view of the cooling sleeve apparatus of FIG. 9 with the cooling body empty;

FIG. 10C is a transverse cross-sectional view of another embodiment of the cooling sleeve apparatus in FIG. 9 with the cooling body filled with fluid and pressed against the coaxial cable; and FIG. 10D is a transverse cross-sectional view of the cooling sleeve apparatus of FIG. 9 with the cooling body empty.

DETAILED DESCRIPTION OF EMBODIMENTS

Figure 1:
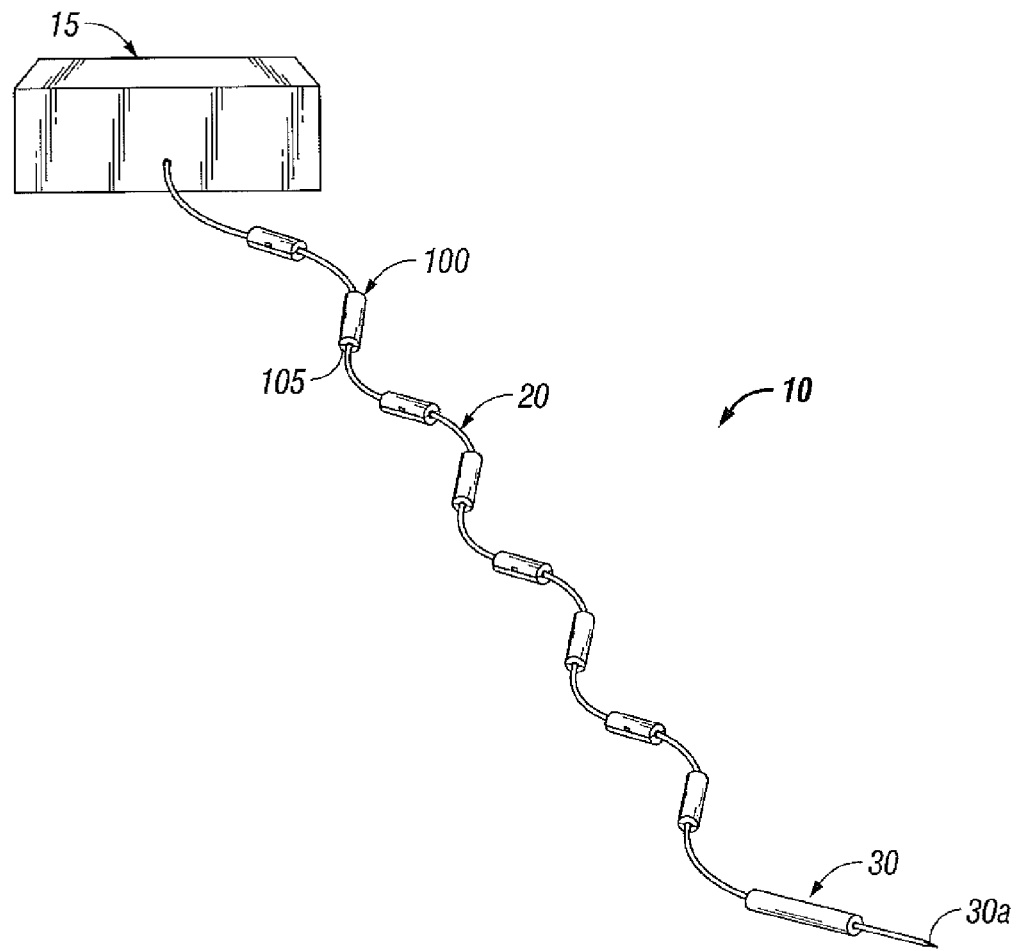
FIG. 1 is an illustration of a system for performing medical/surgical ablation with a plurality of cooling apparatus, according to an embodiment of the present disclosure, disposed on a coaxial cable thereof.

Embodiments of the presently disclosed coaxial cable cooling apparatus will now be described in detail with reference to the drawing figures wherein like reference numerals identify similar or identical elements. As used herein and as is traditional, the term "distal" refers to the portion that is furthest from the user and the term "proximal" refers to the portion that is closest to the user. In addition, terms such as "above", "below", "forward", "rearward", etc. refer to the orientation of the figures or the direction of components and are simply used for convenience of description.

Medical ablation of tissue is increasingly performed using microwave energy. Microwave energy is typically delivered to an electrosurgical energy delivery apparatus, such as a microwave antenna assembly, through a coaxial cable. Referring now to FIG. 1, a system for delivering microwave energy, including at least one coaxial cable cooling apparatus 100 according to an embodiment of the present disclosure, is shown as 10. The microwave delivery system 10 includes a microwave generator 15, a coaxial cable 20 operatively connected or coupled to generator 15, at least one coaxial cable cooling apparatus 100 disposed on coaxial cable 20, and an electrosurgical energy delivery apparatus 30 including at least one microwave antenna 30a capable of transmitting microwave energy.

As seen in FIG. 1, coaxial cable cooling apparatus 100 (hereinafter "cooling apparatus 100") includes a cooling body or housing 105 configured to attach to at least a portion of the coaxial cable 20. At least a portion of the housing 105 is configured to absorb thermal energy from at least a portion of the coaxial cable 20. Housing 105 may include a cooling portion and a thermal dissipation or thermal energy removal portion. Cooling portion may include a passive cooling means, such as, for example, thermal energy absorbing material with a high thermal mass or a thermal energy exchanging means, an active cooling means, such as, for example, fluid cooling, or any suitable combination thereof. Thermal dissipation or thermal energy removal portion may provide a means of removing thermal energy from the coaxial cable 20 and/or cooling apparatus 100. Various passive and active cooling means in accordance with the present disclosure are disclosed hereinbelow.

As seen in FIG. 1, microwave delivery system 10 may include a plurality of cooling apparatuses 100 spaced from each other and disposed on the coaxial cable 20. Positioning and spacing between the cooling apparatuses 100 on the coaxial cable 22 may be dependant on a number of factors. Factors include the thermal energy generated by the coaxial cable 20, the thermal mass of the individual cooling apparatus 100, the thermal energy absorption rate of the individual cooling apparatus 100 and one or more characteristics of the microwave energy, such as, for example, the frequency, phase and power of the microwave energy. The thermal energy generated by the coaxial cable 20 may depend upon the medical procedure including the length of time of the procedure, the energy delivered during the procedure, the type of tissue targeted by the procedure, and the type of device used for the procedure. The number of cooling apparatus 100 may depend on the spacing determined by the factors discussed above and the total length of the coaxial cable 20. In one embodiment, only a single cooling apparatus 100 is utilized.

The position of the hot spots on the coaxial cable 20 may vary and may even move during a procedure thus making placement of the cooling apparatus 100 on an individual hot spot difficult. As an alternative to placing cooling apparatus 100 directly on hot spots, a plurality of cooling apparatus 100 may be placed on coaxial cable 20 to provide uniform cooling of the coaxial cable 20. For example, spacing between hot spots on a coaxial cable may be related to a characteristic of the wavelength, e.g., hot spots may be spaced every half wavelength along the length of the coaxial cable. To provide uniform cooling of the cable, cooling apparatus 100 may be spaced uniformly along the coaxial cable 100 with the center of each cooling apparatus spaced one-half wavelength apart. While each individual cooling apparatus 100 may not be positioned directly on a hot spot, the distance from a cooling apparatus 100 to a hot spot, along the coaxial cable 20, will be uniform.

Passive Cooling

Cables used for transmitting microwave energy are designed for efficient transmission of microwave energy without discharge or loss of microwave energy. Examples of suitable cables include a coaxial cable, a triaxial cable and a double sheathed coaxial cable. Although any suitable cable is contemplated by the present disclosure, in the illustrated embodiment of FIGS. 2A and 2B, a coaxial cable 20 includes an outer sheath 22, an outer conductor 24, an inner conductor 26 and a dielectric 28 between the outer conductor 24 and the inner conductor 26. Efficient transmission of microwave energy, with minimal amount of microwave energy discharge or loss, requires the inner conductor 26 to be positioned at the approximate radial center of the outer conductor 24. The dielectric 24 both positions the inner conductor 26 at the approximate radial center of the outer conductor 24 and insulates the inner conductor 26 and outer conductor 24 by providing a uniform impedance between the inner and outer conductors 26, 24.

The construction of a coaxial cable 20, to efficiently transmit microwave energy, results in a coaxial cable 20 with excellent transmission properties and typically with very little thermal mass. As a result, during electrosurgery using microwave energy, particular amounts of energy discharged within the coaxial cable may elevate the temperature of the coaxial cable to unacceptable levels. Cable heating is more prevalent with small, flexible cables that are needed when manual manipulation of the cable is required such as, for example, during the placement of a delivery apparatus 30.

Figure 2A:
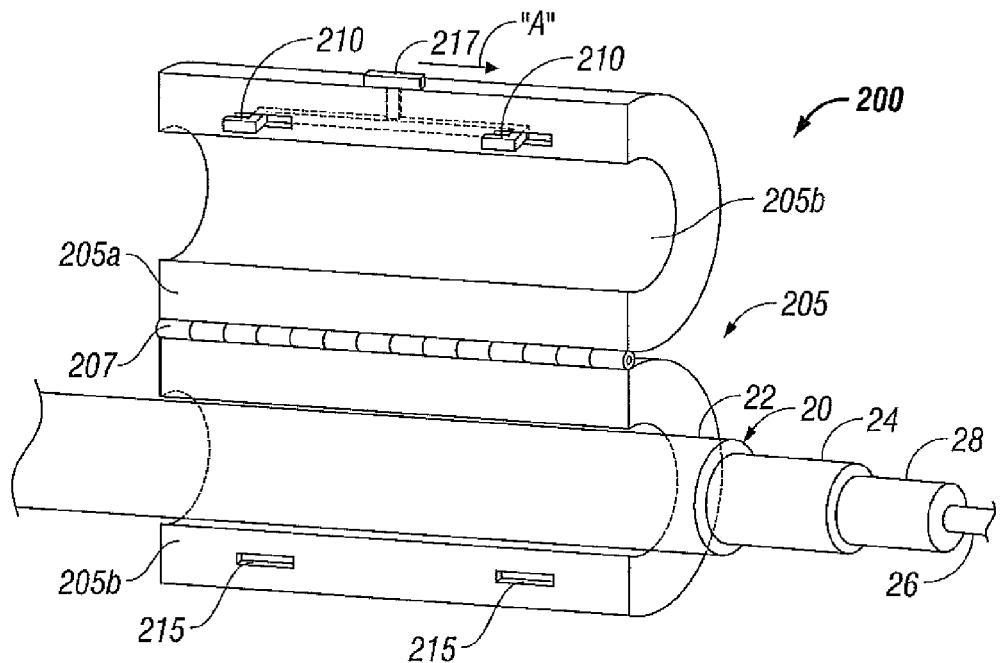
FIG. 2A is a perspective view of a hinged cooling apparatus according to an embodiment of the present disclosure.

With continued reference to FIG. 2A, a cooling apparatus 200, in accordance with an embodiment of the present disclosure, is at least partially disposed on coaxial cable 20. Cooling apparatus 200 includes a cooling body or housing 205 configured to absorb thermal energy from at least a portion of the coaxial cable 20. Housing 205 includes an upper housing portion 205a and a lower housing portion 205b interconnected by a hinge-member 207 (e.g., piano hinge, living hinge, etc.), or other suitable connector. Cooling apparatus 200 may be reusable or disposable and may be either temporarily or permanently attached to the coaxial cable 20.

Cooling apparatus 200 may include an attachment means to affix housing 205 to the coaxial cable 20. As illustrated in FIG. 2A, attachment means may include at least one latch 210 extending from the upper housing portion 205a that enters a corresponding slot 215 formed in the lower housing portion 205b. Attachment means may lock the cooling apparatus 200 onto the coaxial cable 20. A latch release 217 is provided to slide in the direction of the arrow "A" to release latch 210 from slot 215. Others suitable means of attaching the housing 205 onto the coaxial cable may be used.

In accordance with an embodiment of the present disclosure, the cooling apparatus 200 includes a thermal mass that is greater than that of the coaxial cable 20 disposed therewithin. Attaching a cooling apparatus 200 such that cooling apparatus 200 is in thermal contact with the coaxial cable 20 increases the overall thermal mass of the body, i.e., the combined thermal mass of the coaxial cable 20 and the cooling apparatus 200. In use, upper housing portion 205a and/or the lower housing portion 205b may draw thermal energy away from, and thereby cool, the coaxial cable 20. Alternatively, increasing the thermal mass of the body, by attaching one or more cooling apparatus 200, may decrease the rate at which the cable temperature increases.

In use, cooling apparatus 200, while disposed on and absorbing thermal energy from coaxial cable 20, may not alter and/or significantly change the physical properties of the coaxial cable 20, e.g., the spacing and/or positioning of the inner conductor 26, dielectric layer 28 or outer conductor 24 relative to each other. Additionally, cooling apparatus 200 may not alter and/or significantly change the electrical properties of the coaxial cable 20, e.g., cable impedance and/or conductive properties thereof.

As seen in FIG. 2A, an inner surface 205b of the cooling apparatus 200 is configured to contact the sheath 22 of the coaxial cable 20 when cooling apparatus 200 is operatively connected or coupled thereto. In yet another embodiment of the present disclosure, at least a portion of cooling apparatus 200 may pierce the sheath 22 and make direct thermal contact with outer conductor 24. Direct thermal contact between the cooling apparatus 200 and outer conductor 24 may be desirable to increase the rate of thermal energy removal from the coaxial cable 20. Alternatively, a portion of the sheath 22 may be removed to allow direct thermal contact between cooling apparatus 200 and outer conductor 24.

Figure 2B:
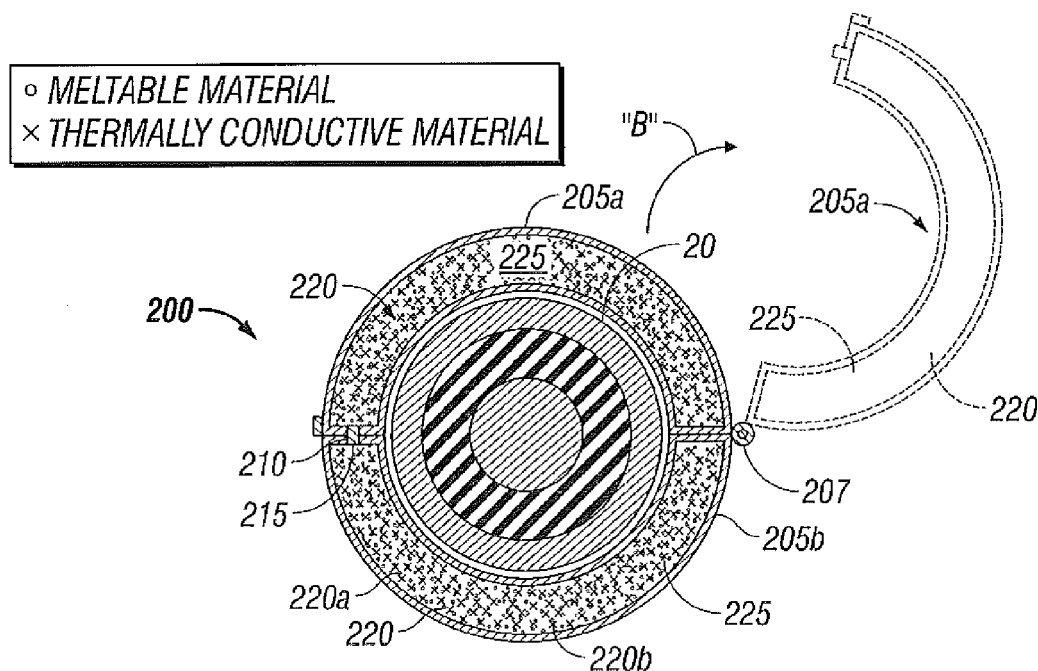
FIG. 2B is a transverse cross-sectional view of the hinged cooling apparatus of FIG. 2A.

FIG. 2B is a traverse cross-sectional view of the cooling apparatus 200 of FIG. 2A with the upper housing portion 205a in an open position (shown in phantom) and in a closed position. In a closed position, the upper housing portion 205a is adjacent the lower housing portion 205b. As indicated by arrow "B", the upper housing portion 205a may pivot relative to the lower housing portion 205b between a closed position and an open position.

To place the cooling apparatus 200 on the coaxial cable 20, the coaxial cable 20 is placed in the upper or lower housing portion 205a, 205b while cooling apparatus 200 is in an open position. The upper and lower housing portions 205a, 205b are then reposition to a closed position and latch 210 in upper housing portion 205a connects with slot 215 in lower housing portion 205b, thereby locking cooling apparatus 200 on coaxial cable 20. Cooling apparatus 200 may be removed from coaxial cable 20 by sliding latch release 217 in the direction of arrow "A" (see FIG. 2A), disengaging latch 210 from slot 215 and repositioning the upper and lower housings 205a, 205b to an open position.

Housing portions 205a, 205b may each define respective cavities 225 for containing material 220 therein, the material 220 having a high thermal mass and/or high energy absorbing properties. In one embodiment, housing 205 may contain a meltable material 220a, such as wax, disposed within the cavity 225 of housing portions 205a, 205b. The meltable material 220a may be solid at room temperature or before cooling apparatus is disposed on the coaxial cable 20. Meltable material may be any suitable material that exhibits a phase change while absorbing thermal energy. Phase change may be from a solid to a liquid, from a liquid to vapor or any other suitable phase change that results in the meltable material absorbing thermal energy. The melting point or temperature at which the phase change of the meltable material 220a occurs should be below any unacceptable high temperature for the coaxial cable 20, Various types of waxes may be suitable because, depending on the specific wax used, the melting point may be between about 40° C. and about 100° C. Cavities 225 of housing portions 205a, 205b may be fluid tight thereby sealing the meltable material 220a therewithin.

In another embodiment, material 220 may include a semi-solid or gel. Cooling may occur as the material evaporates from a semi-solid state to vapor or sublimates from solid to a gel.

Meltable material 220a may be, solid, soft, pliable or formable prior to the application of the cooling apparatus 100 to coaxial cable 20 to allow housing 205 to conform to coaxial cable 20. Alternatively, the meltable material 220a may be granulated, microcapsulated or powderized thus allowing an otherwise hard meltable material 220a to generally conform to the coaxial cable 20. In addition, granulating, microcapsulating or powderizing a meltable material 220a may decrease the individual particle size and increases the overall surface area of the meltable material 220a and may result in an increase in the rate of thermal energy absorption of material 220a.

In another embodiment, material 220 may include a meltable material 220a and at least one thermally conductive material 220b, such as, for example, aluminum or iron. The thermally conductive material 220b may be homogenously mixed with the meltable material 220a such that thermally conductive material 220b distributes the thermal energy throughout the cavities 225 and the meltable material 220a absorbs the thermal energy. The homogenous mixture of a meltable material 220a and a thermally conductive material 220b may result in material 220 with a high thermal mass and a high rate of thermal energy absorption. Addition of the thermally conductive material 220b may evenly distribute the thermal energy throughout cavity 225 of housing portions 205a, 205b.

Alternatively, thermally conductive material may not be homogenously mixed with the meltable material. Instead, thermally conductive material may be positioned within the cavities such that thermal energy is drawn away from the coaxial cable 20, such as, for example, fins similar to that of a heat exchanger.

The meltable material 220a may be a wax selected from a group including insect wax, vegetable wax, mineral wax, animal wax, petroleum wax, synthetic wax and any suitable combination thereof.

Usable insect waxes include but are not limited to beeswax, produced by honey bees, with a melting point between about 61° C.-66° C.; Chinese wax, produced by scale insects such as *Coccus ceriferus* and *Brahmaea japomca* (Coecoidea), with a melting point between about 82° C.-84° C.; wax produced by the *Icerva purchasi* and *Dactylopius coccus*, with a melting point of about 78° C. and between about 99° C.-101° C., respectively; and Shellac, a wax is secreted by the Lac insect, with a melting point between about 74° C.-78° C.

Useful vegetable waxes include but are not limited to Bayberry wax, from the surface of the berries of the bayberry shrub, with a melting point of about 45° C.; Candelilla wax, from the Mexican shrubs *Euphorbia cerifera* and *E. antisyphilitica*, with a melting point between about 67° C.-79° C.; Carnauba wax, from the leaves of the Carnauba palm, with a melting point between about 78° C.-85° C.; Castor wax, formed from hydrogenated castor oil, with a melting point between about 61° C.-69° C.; Japan wax, formed from a byproduct of lacquer manufacture, with a melting point of about 53° C.; Ouricury wax, from the Brazilian Feather palm, with a melting point between about 81° C. and 84° C.; and Rice bran wax, obtained from rice bran, with a melting point between about 77° C.-86° C.

Usable mineral waxes include but are not limited to Montan wax, extracted from lignite and brown coal, with a melting point between about 82° C.-95° C.; and Ozocerite, a naturally occurring wax found in lignite beds, with a melting point between about 58° C.-100° C.

Usable animal waxes include but are not limited to Spermacet, obtained from the head cavities and blubber of the sperm whales and Lanolin, also known as wool wax, obtained from the sebaceous glands of sheep with a melting point between about 35° C.-42° C.

Usable petroleum waxes include but are not limited to Paraffin wax, made of long-chain alkane hydrocarbons, with a melting point between about 47° C.-64° C.; and Microcrystalline wax, produced by de-oiling petrolatum, with a melting point between about 60° C.-80° C.

Usable synthetic waxes including but are not limited to polyethylene waxes, based on polyethylene, and waxes chemically modified such as, for example, esterified or saponified, substituted amide waxes and polymerized a-olefins.

Material 220 may include any suitable material, or mixture of materials, capable of absorbing and retaining a thermal load.

Figure 3A:
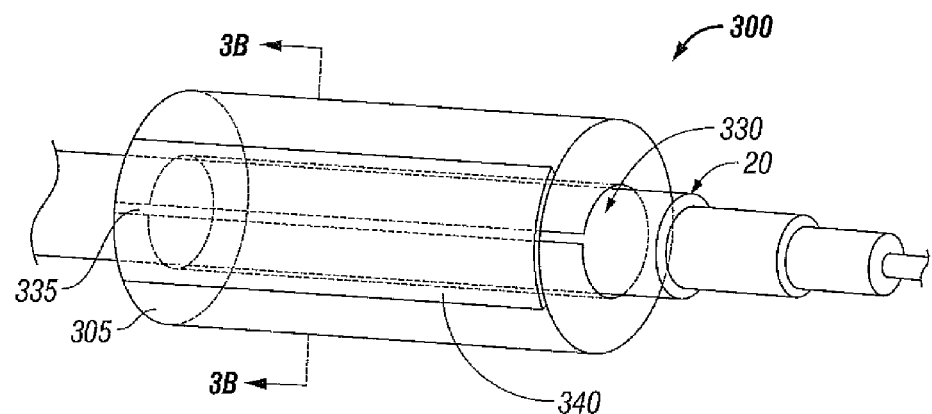
FIG. 3A is a perspective view of a slip-on cooling apparatus according to an embodiment of the present disclosure.
Figure 3B:
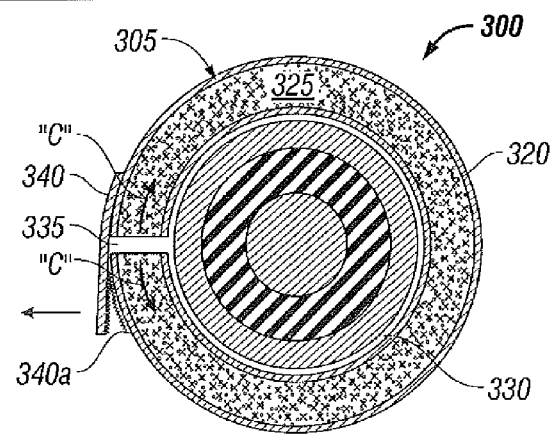
FIG. 3B is a transverse cross-sectional view of the slip-on cooling apparatus of FIG. 3A.

Turning now to FIGS. 3A and 3B, another embodiment of a cooling apparatus 300 of the present disclosure is shown. Cooling apparatus 300 includes a cooling body or housing 305 forming a lumen 330 in the approximate radial center of the cooling housing 305. Access to the lumen 330 is provided by a channel 335 extending through housing 305 and extending an entire length thereof. Housing 305 is sufficiently flexible such that housing 205 can be manipulated to open or expand channel 335, in the direction of the opposing arrows "C", to allow coaxial cable 20 to slip through channel 335 and into lumen 330.

Once coaxial cable 20 is disposed in lumen 330 a flap 340, fastened to housing 305 on one side of channel 335, may be used to close the channel 335 by selectively attaching to housing 305 at a flap attachment area 340a on the second side of channel 335, Flap attachment area 340a may use any suitable attachment means, such as, for example, hook and loop type fasteners, adhesive, tape, snaps, buttons or latches. To remove cooling apparatus 300 from coaxial cable 20 flap 340 is detached from the flap attachment area 340a, channel 335 is opened by pulling the housing 305 in the direction of the opposing arrows "C" and the coaxial cable 20 is removed from lumen 330.

The diameter of lumen 330 is sized to be substantially equal to an outer diameter of the coaxial cable 20 such that when the channel 335 is closed, with the coaxial cable 20 in the lumen 330, the housing 305 makes substantial contact with a length of the coaxial cable 20.

As illustrated in the cross-sectional view in FIG. 3B, housing 305 forms a chamber 325 that contains thermal energy absorbing material 320 as discussed hereinabove. Material may be contained within chamber 325 by a fluid-tight manner.

In yet another embodiment of the present disclosure, an internal surface of the housing 305 within the lumen 330 may pierce the sheath 22 and make thermal contact with the outer conductor 24 to facilitate the removal of thermal energy from the coaxial cable 20.

Figure 4A:
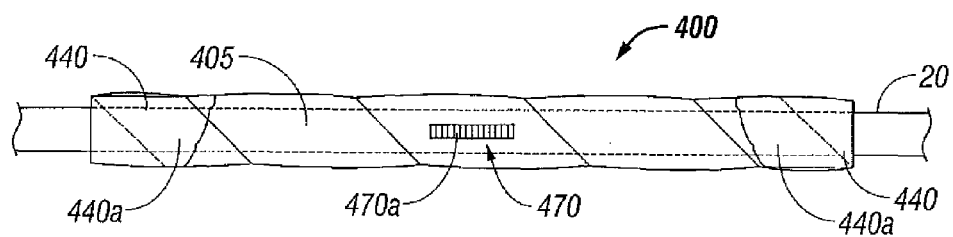
FIG. 4A is plan view of cooling apparatus with an elongate body, according to another embodiment of the present disclosure, disposed on a coaxial cable of the surgical ablation system.
Figure 4B:
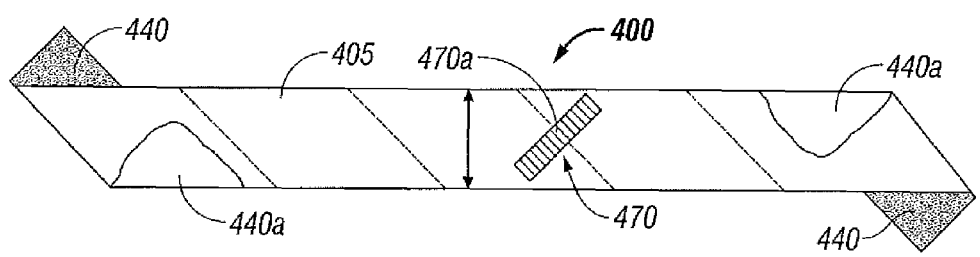
FIG. 4B is a plan view of the cooling apparatus of FIG. 4A.
Figure 4C:
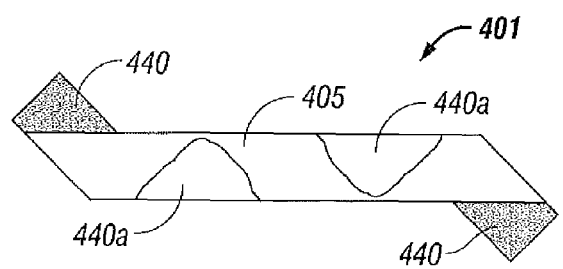
FIG. 4C is a plan view of the cooling apparatus of FIG. 4B with an elongate body configured to form a single wrap on a coaxial cable.

As seen in FIGS. 4A-4C, another embodiment of a cooling apparatus 400 of the present disclosure is shown. Cooling apparatus 400 includes an elongate cooling body 405 in the form of a tape-like structure for wrapping coaxial cable 20. Cooling apparatus 400 may be wrapped along or around coaxial cable 20, as illustrated in FIG. 4A. Cooling apparatus 400 includes a flap 440 on each end of cooling body 405 that attaches to a flap landing area 440a and secures cooling apparatus 400 to the coaxial cable 20. Housing 405 contains thermal energy absorbing material as discussed in the embodiments above.

The length of coaxial cable 20 covered by the cooling apparatus 400 is determined by the width of the cooling body 405, the pitch or angle of the wrap, the amount of overlap between two adjacent wraps, the diameter of the coaxial cable 20 and the length of the cooling apparatus 400. For example, FIGS. 4A and 4B illustrate a cooling apparatus 400 wrapped approximately four times around a coaxial cable 20, with little or no overlap between wraps, at a pitch of approximately 45 degrees. The length of coaxial cable 20 covered by the cooling apparatus 400 may be approximately four times the width of the cooling body 405.

FIG. 4B illustrates an extended or unwrapped cooling apparatus 400 of FIG. 4A. The length and width may be larger or smaller based on the dimensions of coaxial cable covered by the cooling apparatus 400. Increasing the length of cooling apparatus 400 may increase the number of times the cooling apparatus 400 will wrap around the coaxial cable 20. Increasing the width of cooling apparatus 400 may increase the amount of coaxial cable 20 covered by each wrap.

Returning to FIG. 4A, the size of each flap 440 and the size and position of each flap attachment area 440a on the cooling apparatus 400 may be adjusted for different coaxial cable 20 dimensions. For example, the center of the flap 440 and the center of the flap attachment area 440a are spaced such that when the cooling apparatus 400 is wrapped around the coaxial cable 20 the flap 440 folds onto at least a portion of the flap attachment area 440a. The spacing between the flap 440 and the flap attachment area 440a is about equal to, or greater than, the circumference of the coaxial cable 20. Spacing between the flap 440 and the flap attachment area 440a may be adjusted for larger diameter or smaller diameter coaxial cables.

As seen in FIG. 4C, a cooling apparatus 401 is provided and includes a single-wrap around a portion of the coaxial cable. Cooling apparatus 401 may be applied to specific hot-spots in or along the transmission path, such as, for example, connections to the coaxial cable, connections between two coaxial cables and bends or kinks in a coaxial cable.

The cooling apparatus 100, 200, 300, 400 and 401 with passive cooling discussed hereinabove are attached to a coaxial cable 20 thereby increasing the thermal mass of the body. During energy delivery the meltable material, contained therewithin, absorbs energy and may change from a solid state to a melted state. Upon completion of the surgical procedure meltable material may cool to a temperature below the melting point of the meltable material and may re-solidify to a solid state.

During a surgical procedure a cooling apparatus may absorbed an amount of thermal energy such that material in the cooling apparatus melts and coaxial cable and/or cooling apparatus may approach an unacceptable temperature. Clinician may replace the heated cooling apparatus, containing the melted material, with an unheated cooling apparatus, thereby providing additional passive cooling for the coaxial cable. After the surgical procedure, or after heated cooling apparatus is removed from the coaxial cable, cooling apparatus cools and meltable material re-solidifies to a solid-like state.

Returning to FIGS. 4A and 4B, cooling apparatus 400 may contain a temperature sensor 470 to sense the temperature of the cooling apparatus 400. Temperature sensor 470 may include an indicator 470a, such as, for example, a strip-type indicator or other suitable display, to provide the temperature of the cooling apparatus 400 to a clinician. Alternatively, sensor may include an electronic circuit (not explicitly shown) to measure and indicate a temperature. Electronic circuit (not explicitly shown) may include a means to communicate a temperature to a remote system, such as, for example, a computer or other suitable information collection system.

Active Cooling

Figure 5:
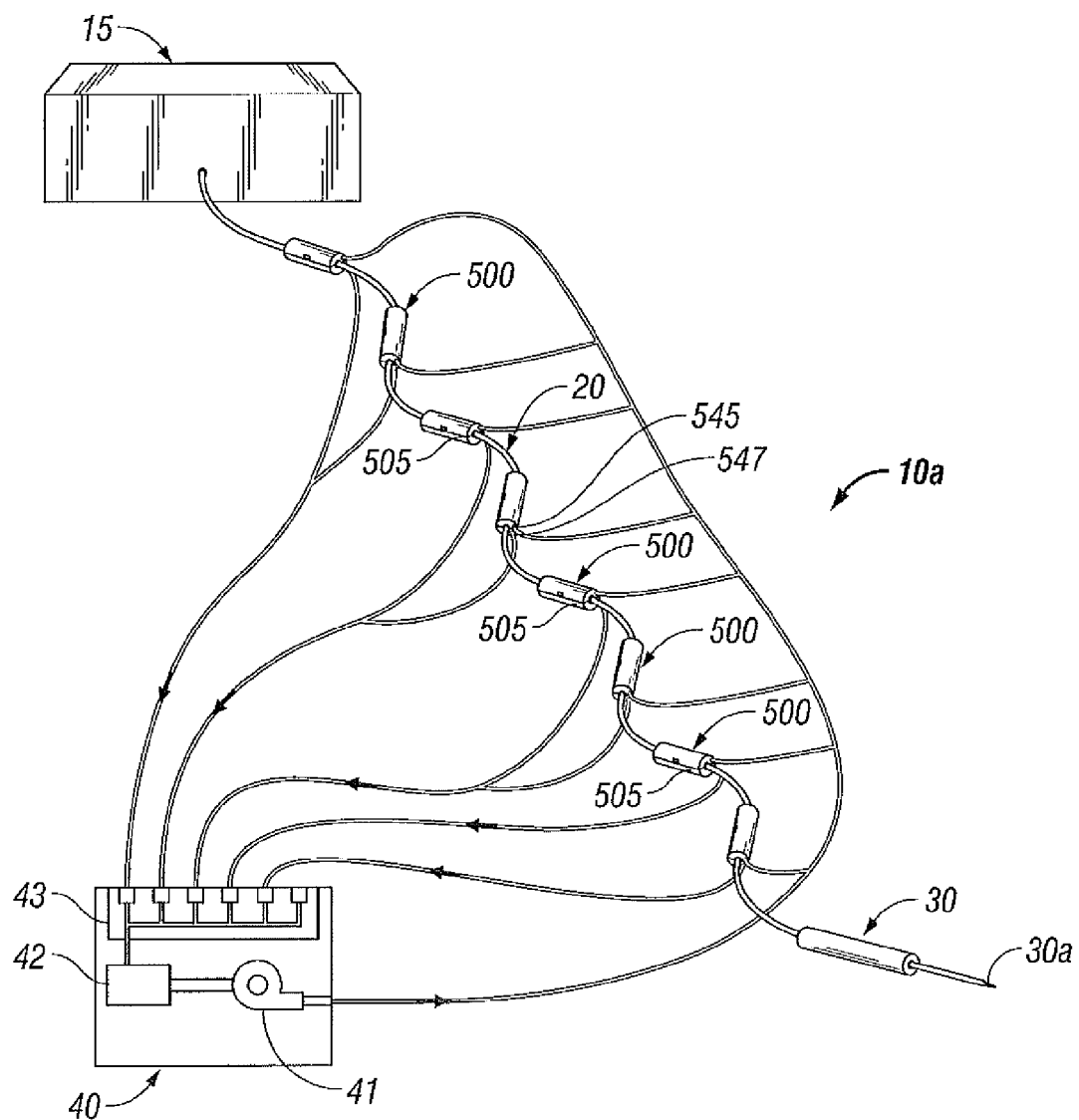
FIG. 5 is an illustration of a system for performing medical/surgical ablation including a plurality of cooling apparatus with fluid cooling, according to an embodiment of the present disclosure, disposed on a coaxial cable of the surgical ablation system.

Referring now to FIG. 5, a system for delivering microwave energy, including at least one cooling apparatus 500 according to an embodiment of the present disclosure, for actively cooling a coaxial cable 20 is shown as 10a. The microwave delivery system 10a includes a microwave generator 15, a coaxial cable 20 with at least one coaxial cable cooling apparatus 500 disposed on the coaxial cable 20, a system 40 for supplying cooling fluid and an electrosurgical energy delivery apparatus 30, including at least one microwave antenna 30a capable of transmitting microwave energy.

Coaxial cable cooling apparatus 500 (hereinafter "cooling apparatus 500") includes a cooling body or housing 505 configured to attached to at least a portion of the coaxial cable 20, at least one inlet member 545, and at least one outlet member 547. The one or more inlet members 545 and one or more outlet members 547 may be disposed in, formed by, or defined by housing 505.

Cooling fluid is supplied to the at least one inlet member 545 by cooling fluid supply 40 and circulated through at least a portion of the housing 505. The fluid circulated therethrough absorbs thermal energy generated by the coaxial cable 20 from the cooling apparatus 500, or any portion therewithin. Alternatively, the fluid circulating therethrough may absorb thermal energy directly from the coaxial cable 20. Fluid is discharged from the housing 505 through the at least one outlet member 547.

Figure 6:
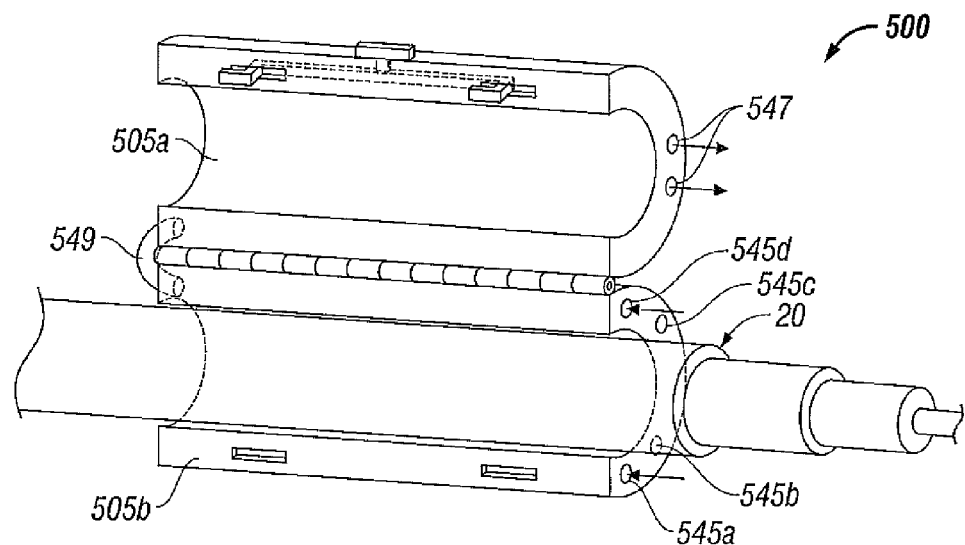
FIG. 6 is a perspective view of the hinged cooling apparatus of FIG. 2A with fluid cooling.

FIG. 6 illustrates a cooling apparatus 500, similar to cooling apparatus 200 of FIG. 2A, with a plurality of inlets 545a-545d disposed in the lower housing 505b. Fluid is delivered to at least one of the inlets 545a-545d and circulated through the lower housing 505b. A jumper hose 549 fluidly inter-connects to upper housing 505a and lower housing 505b to circulate fluid between the upper housing 505a and the lower housing 505b. Fluid is discharged from the cooling apparatus 500 through at least one of the plurality of the outlets 547a-547b disposed in the upper housing 505a. Fluid circulated through housing 505 may absorb thermal energy from at least one of the lower housing 505a, the upper housings 505b and the material contained therewithin. Material may include a material with a high thermal mass and high energy absorbing properties as discussed herein.

Returning to FIG. 5, cooling fluid supply 40 may include a pump 41 for circulating the fluid, a cooling unit 42 for cooling the fluid returned from the cooling apparatus 500 through the return manifold 43. Fluid may be a thermally conductive fluid, such as, for example, water, saline, ammonium chloride, sodium nitrate, potassium chloride or any suitable fluid selected for the intended purpose of dissipating heat.

Figure 7:
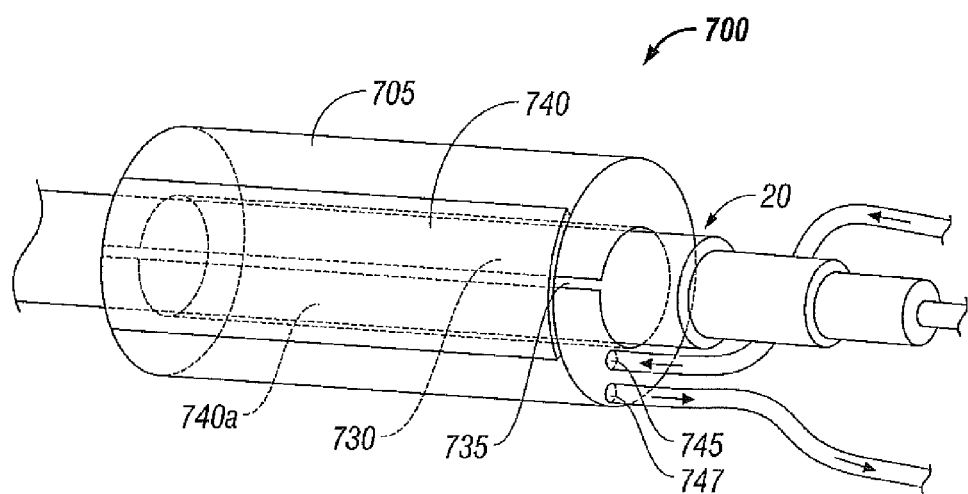
FIG. 7 is a perspective view of the slip-on cooling apparatus of FIG. 3A with fluid cooling.

FIG. 7 illustrates yet another embodiment of a cooling apparatus 700 of the present disclosure. Cooling apparatus 700 includes a cooling body or housing 705, defining an inner lumen 730 and a channel 735, and an inlet 745 and an outlet 747 formed in the housing 705. Flap 740 connects to the housing 705 on one side of the channel 735 and attaches to flap attachment area 740a on housing 705 on the opposite side of channel 735.

Cooling fluid is supplied to inlet 745 of housing 705, circulated through housing 705 before being discharged through outlet 747. Cooling fluid may be circulated through a portion of the housing 705 adjacent to and in thermal communication with the coaxial cable 20 to absorb thermal energy therefrom.

Figure 8A:
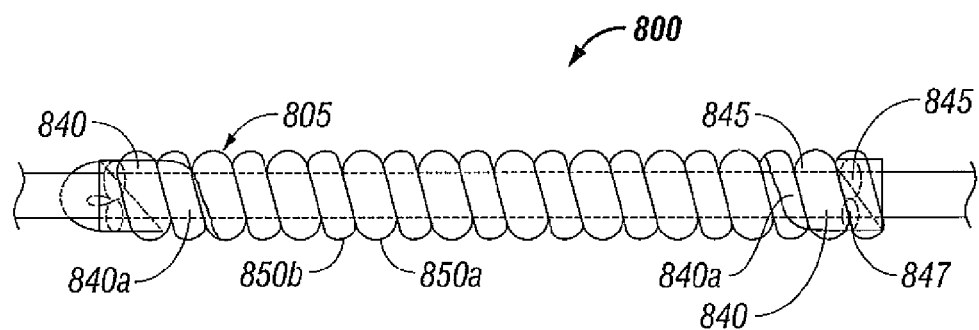
FIG. 8A is plan view of a multi-lumen cooling apparatus, according to an embodiment of the present disclosure, disposed on a coaxial cable of the surgical ablation system.
Figure 8B:
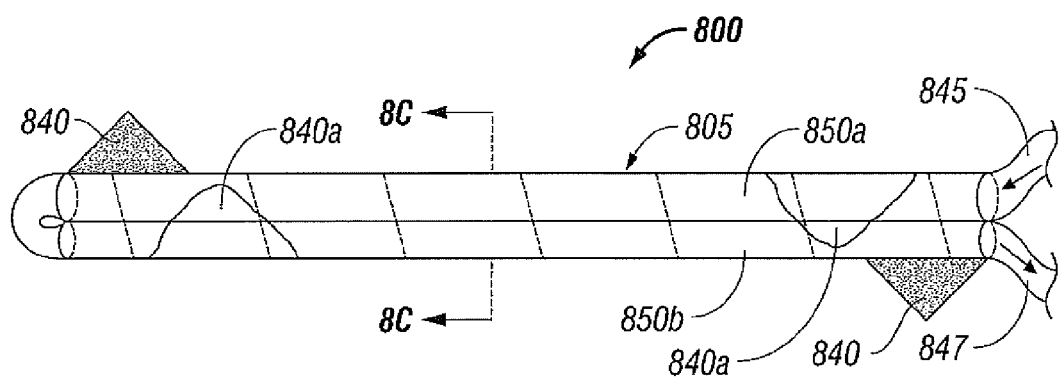
FIG. 8B is a plan view of the multi-lumen cooling apparatus of FIG. 8A.
Figure 8C:
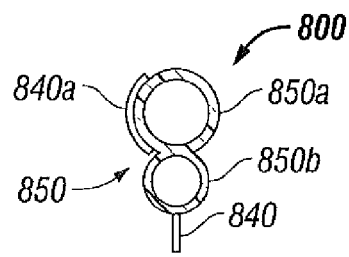
FIG. 8C is a transverse cross-sectional view of the multi-lumen cooling apparatus of FIG. 8B as taken through 8C-8C of FIG. 8B.

Turning now to FIGS. 8A-8C, yet another embodiment of a cooling apparatus 800, according to the present disclosure is shown. Cooling apparatus 800 includes a cooling body, or housing 805, having at least two tubes 850a, 850b, one or more attachment flaps 840, and defining one or more flap attachment areas 840a. An inlet member 845 and an outlet member 847 may be fluidly connected to, or are integrally formed with, cooling tube 850a and return tube 850b, respectively. Fluid is supplied to inlet member 845 and is circulated though cooling tube 850a and return tube 850b. Thermal energy from the coaxial cable 20 and/or the cooling apparatus 800 is absorbed by the cooling fluid and is discharged through return tube 850b.

With reference to FIG. 8A, cooling apparatus 800 is disposed on a coaxial cable 20. Cooling apparatus 800 is wrapped around the coaxial cable 20. Cooling apparatus 800 is secured on each end by flaps 840 that selectively attach to flap attachment areas 840a.

The absorption rate of thermal energy from the coaxial cable 20 by cooling apparatus 800 is dependant on several factors. One factor is the contact surface area between the cooling and return tubes 850a, 850b and coaxial cable 20. The contact surface area between the cooling and return tubes 850a, 850b may be increased by forming cooling and return tubes 850a, 850b from flexible and/or malleable material such that when disposed on coaxial cable 20 the cooling and return tubes 850a, 850b conform to the surface of the coaxial cable 20. Cooling and return tubes 850a, 850b may be formed from any suitable tubing such as, for example, medical tubing and paratubes. Alternatively, cooling tube 850a may be formed from a suitable material that conforms to the coaxial cable 20 and the return tube 850b, which carries fluid already heated in the cooling tube 850a, may be formed from a suitable material that does not conform to the coaxial cable.

In another embodiment of the present disclosure, the cooling tube 850a contacts the coaxial cable 20 and the return tube 850b is spaced away from the coaxial cable 20, thereby not making contact with the coaxial cable 20.

In yet another embodiment of the present disclosure, the at least one or more tubes 850a, 850b may be formed from multi-lumen tubing made from various materials such as, for example, polytetrafluoroethylene (PTFE), such as the material sold under the trademark Teflon™ and available from DuPont, perfluoroalkoxy (PFA), polytetrafluoroethylene (FEP) or expanded PTFE (ePTFE). The lumens of the multi-lumen tubing may be within one another, concentric, and/or separate and connected.

FIG. 8C is a transverse cross-sectional view of the cooling apparatus 800 of FIG. 8B formed from a multi-lumen tube 850. Multi-lumen tube 850 forms a cooling tube 850a and a return tube 850b with at least one common wall shared therebetween.

Figure 9:
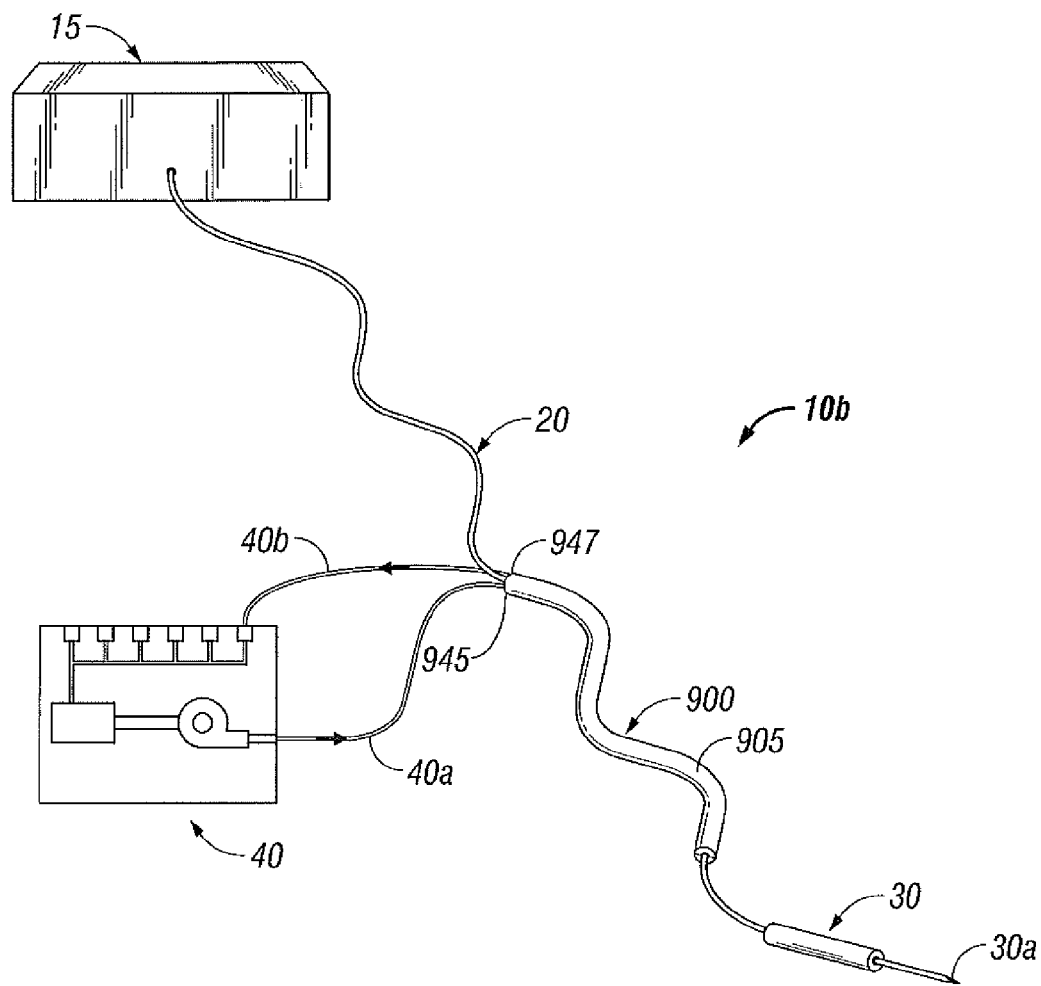
FIG. 9 is a perspective view of a system for performing medical/surgical ablation with a cooling sleeve apparatus, according to yet another embodiment of the present disclosure, disposed on the coaxial cable of the surgical ablation system.

Referring now to FIG. 9, a system for delivering microwave energy, including at least one coaxial cable cooling sleeve apparatus 900, according to an embodiment of the present disclosure, for actively cooling a coaxial cable 20 is shown as 10b. The microwave delivery system 12 includes a microwave generator 15, a coaxial cable 20 with at least one coaxial cable cooling sleeve apparatus 900 disposed on the coaxial cable 20, a system 40 for supplying cooling fluid and an electrosurgical energy delivery apparatus 30, including at least one microwave antenna 30a, capable of transmitting microwave energy.

Coaxial cable cooling sleeve apparatus 900 (hereinafter "cooling sleeve apparatus") includes a cooling body 905, configure to surround at least a portion of coaxial cable 20, at least one inlet 945, and at least one outlet 947.

Cooling fluid is supplied to the at least one inlet 945 by cooling fluid supply 40 via a conduit 40a and circulated through at least a portion of the cooling body 905. Fluid circulated through cooling body 905, absorbs thermal energy generated by the coaxial cable 20 and/or from the cooling apparatus 900, and/or any portion therewithin. The heated fluid is discharged through the outlet 947 via conduit 40b.

As seen in FIGS. 10A-10B and FIGS. 10C-10D, transverse cross-section views of two embodiments of the cooling sleeve apparatus 900 of FIG. 9 are illustrated. In FIGS. 10A and 10B, the housing 905 of a cooling sleeve apparatus 901 forms inner and outer concentric portions 951a, 951b, respectively, each forming at least one fluid tight chamber therewithin. In FIGS. 10C and 10D, the housing 905 of a cooling sleeve apparatus 902 forms a cooling portion 951c and a return portion 951d, each defining a fluid-tight chamber therewithin. In FIGS. 10A and 10C, the fluid-tight chambers are filled with fluid thereby pressing the inner surface 905b of the housing 905 into the coaxial cable 20. Inner surface 905b may be flexible and/or stretchable such that inner surface 905b of the housing 905 and the outer surface 905a of the coaxial cable 20 form suitable thermally conductive contact with one another.

With reference to FIG. 9 and FIGS. 10A-10D, the inlet 945 connects to the inner concentric portion 951a of the cooling apparatus 901 in FIGS. 10A and 10B, or to the cooling portion 951c of the cooling apparatus 902 in FIGS. 10C and 10D, and supplies cooling fluid thereto. The outlet 947 connects to the outer concentric portion 951b of the cooling apparatus 901 in FIGS. 10A and 10B, or to the return portion 951d of the cooling apparatus 902 in FIGS. 10C and 10D. Fluid enters housing 905 through the inlet member 945 and is circulated distally through the inner concentric portion 951a or the cooling portion 951c and absorbs thermal energy generated by the coaxial cable 20. In the distal portion of the cooling apparatus 900 fluid passes from the inner concentric portion 951a to the outer concentric portion 951b, or from the cooling portion 951c to the return portion 951d, through openings therebetween (not explicitly shown). Fluid then flows proximally through the outer concentric portion 951b or the return portion 951d and is discharged through the outlet 947.

In FIGS. 10B and 10D the fluid-tight chambers are not fluid-filled thereby defining a space or cavity 960 between the inner surface 905b of the housing 905 and the coaxial cable 20. The shape of the cooling sleeve apparatus 901, 902 may be defined by a rigid or semi-rigid outer surface 905a of housing 905. The shape may be maintained by the outer surface 905a after a majority of the fluid is removed. Removal of fluid from the housing 905 may create a vacuum therewithin and may pull the inner surface 905b of the housing 905 toward the outer surface 905a thereby increasing the size or volume of space or cavity 960 between the inner surface 905b of the housing 905 and the coaxial cable 20. Space 960 may be sufficiently large to allow the coaxial cable 20 to be threaded or inserted through space 960 thus providing a means of attaching the cooling apparatus 901, 902 to the coaxial cable 20.

The present application discloses apparatus and methods for cooling coaxial cables. It is envisioned that the various embodiments described hereinabove may be combined. For example, elements of the passive cooling apparatus may be applied to the various active cooling apparatus. While the embodiments contained herewithin are described in the context of cooling coaxial cables transmitting microwave energy any apparatus or method may be used to cool any cable, wire or elongated member. Modification of the above-described apparatuses and methods, and variations of aspects of the disclosure that are obvious to those of skill in the art are intended to be within the scope of the claims.

What is claimed is:
1. A cable cooling apparatus for dissipating heat generated by a cable, the cooling apparatus comprising:
a housing defining a fluid-tight cavity therewithin and configured to retain a meltable material in a first state, the housing disposed on at least a portion of a cable and configured to cool at least a portion of the cable, the housing including:

at least one inlet configured to receive a fluid in the housing; and at least one outlet in fluid communication with the at least one inlet for discharging the fluid from the housing;

the meltable material configured to absorb thermal energy during transformation to a second state;

wherein the fluid enters the housing through the inlet and wherein the fluid is circulated through at least a portion of the housing and absorbs thermal energy generated from at least a portion of the cable.

2. The apparatus of claim 1, wherein the housing surrounds at least a portion of the cable.

3. The apparatus of claim 1, wherein the housing further includes:

a cooling portion in thermal communication with the cable; and a return portion for returning fluid through the at least one outlet.

4. The apparatus of claim 1, wherein the cable is a microwave transmission cable.

5. A cable cooling apparatus for dissipating heat generated by a cable, the cooling apparatus comprising:

a housing defining a fluid-tight cavity therewithin, the housing disposed on at least a portion of a cable and configured to cool at least a portion of the cable, the housing including:

at least one inlet configured to receive a fluid in the housing; and at least one outlet in fluid communication with the at least one inlet for discharging the fluid from the housing;

wherein the fluid enters the housing through the inlet and wherein the fluid is circulated through at least a portion of the housing and absorbs thermal energy from at least a portion of the cable.

6. The apparatus of claim 5, wherein the housing surrounds at least a portion of the cable.

7. The apparatus of claim 5, wherein the housing further includes:

a cooling portion in thermal communication with the cable; and a return portion for returning fluid through the at least one outlet.

8. The apparatus of claim 5, wherein the cable is a microwave transmission cable.

9. A method for cooling a microwave energy transmission cable during energy transmission through the cable, the method comprising the steps of:

positioning at least one cable cooling apparatus adjacent a microwave energy transmission cable;

transmitting energy through the energy transmission cable;

circulating a cooling fluid through the at least one cooling apparatus, and dissipating heat produced by the energy transmission cable, during the energy transmission, through the at least one cable cooling apparatus.

10. The method of claim 9 wherein the positioning step includes the step of uniformly positioning a plurality of cable cooling apparatus along the microwave energy transmission cable.

* * * * *